United States Patent
Ohnuma et al.

(10) Patent No.: US 6,409,342 B1
(45) Date of Patent: Jun. 25, 2002

(54) GLAUCOMA DIAGNOSIS APPARATUS AND RECORDING MEDIUM FOR GLAUCOMA DIAGNOSIS

(75) Inventors: Kazuhiko Ohnuma, Sodegaura; Yasufumi Fukuma; Hidetaka Aeba, both of Tokyo, all of (JP)

(73) Assignee: Kabushiki Kaisha Topcon, Tokyo (JP)

( * ) Notice: Subject to any disclaimer, the term of this patent is extended or adjusted under 35 U.S.C. 154(b) by 26 days.

(21) Appl. No.: 09/698,039

(22) Filed: Oct. 30, 2000

(30) Foreign Application Priority Data

Oct. 28, 1999 (JP) .......................................... 11-306494

(51) Int. Cl.[7] ................................................ A61B 3/14
(52) U.S. Cl. ...................................................... 351/206
(58) Field of Search ................................. 351/205, 206, 351/207, 213, 215, 221; 600/476, 477, 558, 561; 356/456; 250/461.2

(56) References Cited

U.S. PATENT DOCUMENTS 5,152,295 A * 10/1992 Kobayashi et al. ......... 351/206
6,198,532 B1 * 3/2001 Cabib et al. ................. 356/456

OTHER PUBLICATIONS

R. W. Knighton, et al., Investigative Opthalmology & Visual Science, vol. 30, No. 11, pp. 2393 to 2402, "The Spectral Reflectance of the Nerve Fiber Layer of the Macaque Retina", Nov. 1989.

* cited by examiner

*Primary Examiner*—George Manuel
(74) *Attorney, Agent, or Firm*—Oblon, Spivak, McClelland, Maier & Neustadt, P.C.

(57) ABSTRACT

A glaucoma diagnosis apparatus capable of minimizing the difficulty of early glaucoma diagnosis caused by the illumination irregularities of the fundus is provided. For each part of the fundus image FB photographed by a color fundus camera Q, the G-component image data corresponding to the G-component reflected light intensity or the B-component image data corresponding to the B-component reflected light intensity is divided by the sum of the G-component image data, the B-component image data and also the R-component image data corresponding to the R-component reflected light intensity, reflected light intensity ratio data is obtained. Based on this reflected light intensity ratio data, the fundus image is reconstructed for glaucoma diagnosis.

13 Claims, 6 Drawing Sheets

GLAUCOMA DIAGNOSIS APPARATUS AND RECORDING MEDIUM FOR GLAUCOMA DIAGNOSIS

BACKGROUND OF THE INVENTION

Field of the Invention

The present invention relates to a glaucoma diagnosis apparatus and a recording medium for glaucoma diagnosis suitably used for early glaucoma diagnosis. In the field of medical science, the glaucoma is considered a disease accompanied by the loss of the bundle of fibers of the optic nerve due to a high intra-ocular pressure or the like. For the purpose of glaucoma diagnosis, a color fundus image has conventionally been photographed using the color fundus camera.

The optic nerve fiber layer has a tendency to reflect much more green light (G component of light) and blue light (B component of light). Especially, it reflects the G component of light in a higher proportion than the other component of light. In the case where an image is displayed only with the G or B component, therefore, the brightness of the image of the fundus area (fundus portion) having the loss of the optic nerve fiber layer is lower than the fundus area having the normal optic nerve fiber layer. The fundus image displayed with the G component or the B component is compared with the surrounding areas, and if there is any darker part in the fundus area, the particular part can be diagnosed as an area where the optic nerve fiber layer may be lost. The thicker the optic nerve fiber layer is, the larger amount of the reflected light of the G or B component is obtained. On the other hand, the red light (R component of light) has a tendency to be reflected less by the optic nerve fiber layer than by the fundus tissue which is located much deeper position than the optic nerve fiber layer.

The aforementioned fact will be explained with reference to the thesis entitled "The Spectral Reflectance of the Nerve Fiber Layer of the Macaque Retina", pp. 2393–2402, Investigative Ophthalmology and Visual Science, Vol. 30, No. 11, November 1989.

FIG. 7 is a diagram showing a model of a fundus image. In FIG. 7, areas A to C and G are where the optic nerve fiber layer normally exists, and areas D to F are where the optic nerve fiber layer is intentionally removed. These areas A to G are irradiated with light or different wavelengths, respectively, all the light reflected from each one of the areas A to G is received, and the total reflectivity for each area with the wavelength as a parameter is plotted in a graph shown in FIG. 8.

In FIG. 8, the left end indicates the reflectivity of blue light, the right end the reflectivity of red light, and the middle point the reflectivity of green light. As apparent from FIG. 8, the reflectivity of red light is larger than that of the light shorter in wavelength.

The reflectivity of only the optic nerve fiber layer for the areas A, B and C is plotted in the graph of FIG. 9. It is read in FIG. 9 that the reflectivity is gradually reduced as the position moves from area A to area C. This is considered due to the fact that the reflectivity is high at the papilla where the optic nerve fiber are concentrated and having increased thickness, which has increased density of the optic nerve fiber, while the thickness and the density of the optic nerve fiber are reduced with the distance from the papilla. Thus it is read that there is a correlation between the thickness of the optic nerve fiber and the reflectivity.

The progress of glaucoma leads to blindness, and therefore, early detection of glaucoma is of urgent necessity. Since the thickness of the optic nerve fiber layer on the fundus varies from one part to another, the fundus image of even a healthy person photographed and displayed in G and B components develops a gradation and it is difficult to determine at first glance whether an area exists or not where the optic nerve fiber layer is lost.

In view of this, a diagnosis technique has been proposed in which an image processing in which two concentric circles of different radii are plotted around the papilla on the fundus image, and with the first circle as an origin, the image data of the G and B components are integrated (or the finite sum is taken) along the radial direction to the second circle, so that a small change in the amount of reflected light caused by the area where the optic nerve fiber layer is lost is replaced by a large change and displayed as a graph taking advantage of the fact that the optic nerve fiber layer is extended substantially radially from the papilla. Based on this graph it is determined whether there exists an area where the optic nerve fiber layer is lost on the fundus.

The illumination of the fundus, however, develops illumination irregularities at various points, which may cause a gradation with a dark image even in the fundus area having the optic nerve fiber layer. In such a case, it becomes harder to distinguish a fundus area where an optic nerve fiber layer exists from another fundus area where the optic nerve fiber layer is lost. Especially in the initial stage of progress of glaucoma when the optic nerve fiber layer is lost only slightly, illumination irregularities makes it difficult to determine whether a particular patient is going to suffer from glaucoma or not.

Especially, the sign of the chronic loss of optic nerve fiber layer cannot be caught at first glance, and therefore the possibility of the disease cannot be determined.

SUMMARY OF THE INVENTION

The present invention has been achieved in view of the situation described above, and the object thereof is to provide a glaucoma diagnosis apparatus capable of substantially overcoming the difficulty of early glaucoma diagnosis caused by the illumination irregularities of the fundus.

According to first aspect of the invention, a glaucoma diagnosis apparatus characterized in that the glaucoma is diagnosed based on reflected light intensity ratio data which are obtained by division calculation such that the image data corresponding to the reflection intensity of the light of short wavelength is divided by the image data corresponding to the reflection intensity of the light of longer wavelength for each part of the fundus image photographed by a color fundus camera is provided.

According to second aspect of the invention, a glaucoma diagnosis apparatus characterized in that the glaucoma is diagnosed based on reflected light intensity ratio data which are obtained by division calculation such that the image data corresponding to the reflection intensity of the light of short wavelength is divided by the image data corresponding to the reflection intensity of the light including longer wavelength for each part of the fundus image photographed by a color fundus camera is provided.

According to third aspect of the invention, a glaucoma diagnosis apparatus characterized in that the glaucoma is diagnosed based on reflected light intensity ratio data which are obtained by division calculation such that G component image data corresponding to the reflection intensity of the G component of light or B component image data corresponding to the reflection intensity of the B component of light is divided by sum of said G component image data, said B component image data and R component image data corresponding to the reflection intensity of the R component of light for each part of the fundus image photographed by a color fundus camera is provided.

According to fourth aspect of the invention, a glaucoma diagnosis apparatus characterized in that the glaucoma is diagnosed based on reflected light intensity ratio data which are obtained by division calculation such that G component image data corresponding to the reflection intensity of the G component of light or B component image data corresponding to the reflection intensity of the B component of light is divided by R component image data corresponding to the reflection intensity of the R component of light for each part of the fundus image photographed by a color fundus camera is provided.

According to fifth aspect of the invention, a glaucoma diagnosis apparatus characterized by comprising arithmetic means for calculating the reflected light intensity ratio data which are obtained by division calculation such that G component image data corresponding to the reflection intensity of the G component of light or B component image data corresponding to the reflection intensity of the B component of light is divided by sum of said G component image data, said B component image data and R component image data corresponding to the reflection intensity of the R component of light for each part of the fundus image photographed by a color fundus camera in order to make a glaucoma diagnosis is provided.

According to sixth aspect of the invention, a glaucoma diagnosis apparatus characterized by comprising arithmetic means for calculating the reflected light intensity ratio data which are obtained by division calculation such that G component image data corresponding to the reflection intensity of the G component of light or B component image data corresponding to the reflection intensity of the B component of light is divided by R component image data corresponding to the reflection intensity of the R component of light for each part of the fundus image photographed by a color fundus camera in order to make a glaucoma diagnosis is provided.

In the glaucoma diagnosis apparatus according to one of the above described aspects, the image data for each part of the fundus is replaced with the reflection intensity ratio (corresponding to the reflectivity ratio) for each part of the fundus and thus the image data is reconstructed, therefore, the adverse effect of illumination irregularities can be obviated.

According to seventh aspect of the invention, a glaucoma diagnosis apparatus characterized by said fundus image photographed by the fundus camera is an image obtained by white light illumination is provided.

With the glaucoma diagnosis apparatus according to the seventh aspect of the invention, the arithmetic process can be simplified.

According to eighth aspect of the invention, a glaucoma diagnosis apparatus characterized by said area of each part of the fundus image corresponds to the area of each pixel of CCD is provided.

With the glaucoma diagnosis apparatus according to the eighth aspect of the invention, the area where the optic nerve fiber layer is lost can be determined in fine detail for each pixel.

According to ninth aspect of the invention, a glaucoma diagnosis apparatus characterized by said glaucoma is diagnosed by an image processing with removing blood tube portion in the fundus image is provided.

With the glaucoma diagnosis apparatus according to the ninth aspect of the invention, the glaucoma can be diagnosed by an image processing with removing the blood tube portion of the fundus image, and therefore the diagnosis can be easily accomplished by displaying the image.

According to tenth aspect of the invention, a glaucoma diagnosis apparatus characterized by said image processing is performed in such a manner that two concentric circles of different radii are plotted along the radial direction about the papilla and the reflected light intensity ratio data are integrated along the radial direction to the second circle with the first circle as an origin is provided.

In the tenth aspect of the invention, a small change in the reflected light amount caused by the area where the optic nerve fiber layer is lost is replaced with a large change by integration and can be displayed as a graph.

According to eleventh aspect of the invention, a recording medium for glaucoma diagnosis wherein a program is recorded for calculating reflected light intensity ratio data which are obtained by division calculation such that G component image data corresponding to the reflection intensity of the G component of light or B component image data corresponding to the reflection intensity of the B component of light is divided by sum of said G component image data, said B component image data and R component image data corresponding to the reflection intensity of the R component of light for each part of the fundus image photographed by a color fundus camera is provided.

According to twelfth aspect of the invention, a recording medium for glaucoma diagnosis wherein a program is recorded for calculating reflected light intensity ratio data which are obtained by division calculation such that G component image data corresponding to the reflection intensity of the G component of light or B component image data corresponding to the reflection intensity of the B component of light is divided by R component image data corresponding to the reflection intensity of the R component of light for each part of the fundus image photographed by a color fundus camera is provided.

DESCRIPTION OF THE PREFERRED EMBODIMENTS

Figure 1:
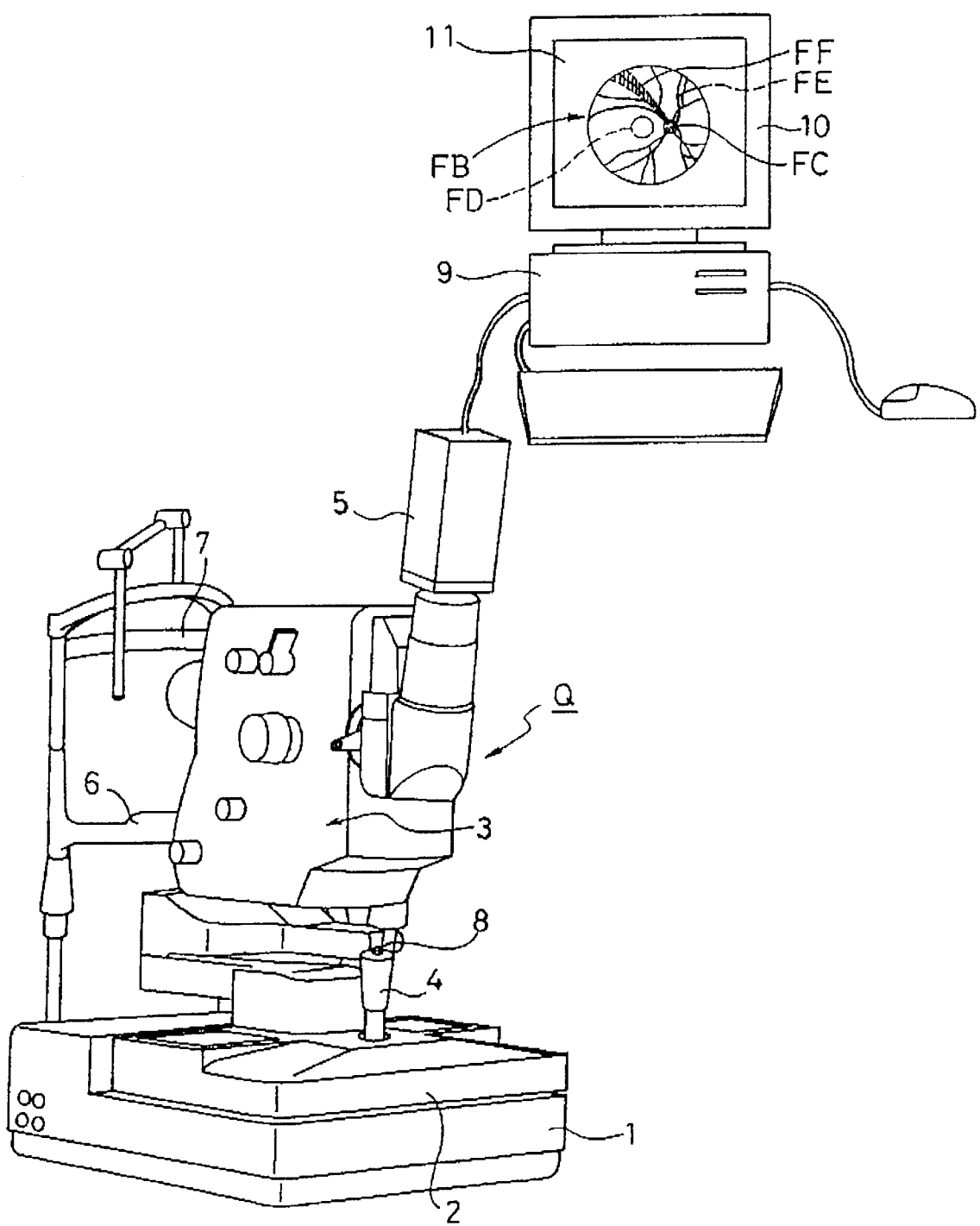
FIG. 1 is a diagram showing an external appearance of an example of a fundus camera used for photographing a fundus image.

FIG. 1 shows an example of a fundus camera Q used for the glaucoma diagnosis apparatus according to this invention. In FIG. 1, reference numeral 1 designates a base, numeral 2 a pedestal, numeral 3 an apparatus body, numeral 4 a joystick, numeral 5 a TV camera, numeral 6 a chin rest, and numeral 7 a forehead stop. The configuration of these parts is well known.

In this fundus camera, a patient, with his chin placed on the chin rest 6 and his forehead applied to the forehead stop 7 is caused by an internal fixation lamp to fix his eye in a predetermined direction, and then an imaging switch 8 is operated, the fundus of the patient's eye to be inspected is illuminated, and a fundus image is photographed by the TV camera 5.

The TV camera 5 is connected to a personal computer 9, for example, comprising a glaucoma diagnosis apparatus, and the fundus image is stored in the frame memory of the personal computer 9. The fundus image can be stored in a hard disk, a magnetic disk, a floppy disk or a magneto-optical disk instead of the frame memory of the personal computer 9.

The personal computer 9 is connected with an image display monitor 10. The stored fundus image FB is displayed on a screen 11 by operating such means as a mouse or a keyboard.

Figure 2:
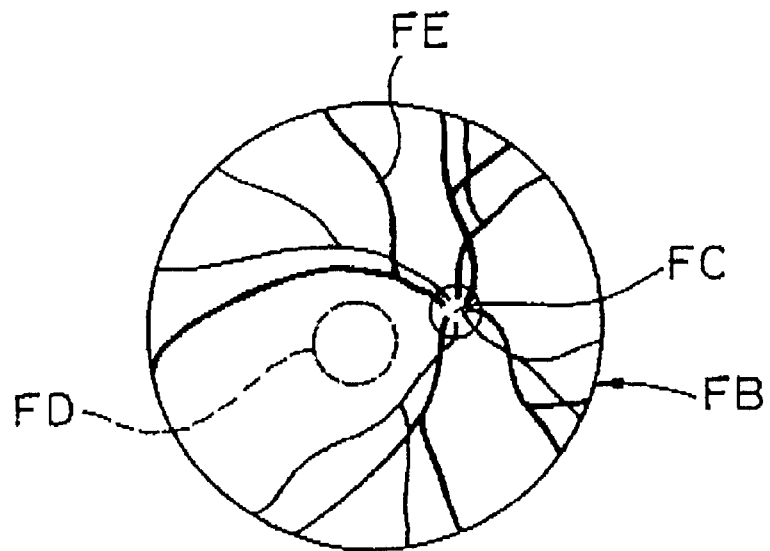
FIG. 2 is a diagram schematically showing an example of a fundus image before being processed.

FIG. 2 shows an example of the fundus image FB photographed by the fundus camera shown in FIG. 1. The fundus image is assumed being displayed only with the G component. It also assumed that the fundus image FB photographed shows that the patient has a fundus lacking the optic nerve fiber layer and is in his early stage of glaucoma, and that the loss of the optic nerve fiber layer is about to such a degree that the area where the optic nerve fiber layer is lost cannot be recognized in the image display using only the G component as the shade cannot be discriminated under the influence of the illumination irregularities. In FIG. 2, therefore, the area where the optic nerve fiber layer is lost is not shown. In FIG. 2, character FC designates the optic nerve papilla, character FD a yellow spot and character FE blood tubes.

The loss of the optic nerve fiber layer should proportionately reduce the reflectivity of the G or B component. The reason is that the optic nerve fiber layer reflects the G or B component in a ratio higher than the R component.

Therefore, determining the reflectivity of the G and B components for each part of the fundus is an idea. It is substantially impossible, however, to determine the reflectivity itself for each part of the fundus.

This is because of the fact that although the reflectivity is generally defined by dividing the reflected light amount by the incident light amount as well known, it is difficult to measure the incident light amount for each part of the fundus, and the illumination irregularities makes it impossible to handle the incident light amount uniformly for each part of the fundus.

This leads us to the concept of the reflectivity ratio equivalent (reflected light intensity ratio) for each part of the fundus. The concept of the reflectivity ratio equivalent will be explained below.

The incident light amount (incident light intensity) to an arbitrary part of the fundus for the R, G and B components are designated by $Ir$, $Ig$ and $Ib$, respectively, the reflectivity at the particular arbitrary parts by $Rr$, $Rg$, $Rb$, respectively, and the reflected light amount (reflected light intensity) from the particular arbitrary part by $Irr$, $Irg$, $Irb$. For the R, G and B components, the following equations are made.

$$Irr = Ir \times Rr \text{ (equation indicating the reflected light amount for the R component)} \quad (1)$$

$$Irg = Ig \times Rg \text{ (equation indicating the reflected light amount for the G component)} \quad (2)$$

$$Irb = Ib \times Rb \text{ (equation indicating the reflected light amount for the B component)} \quad (3)$$

where the reflected light amount $Irr$, $Irg$, $Irb$ of the R, G, B components, respectively, correspond to measured values obtained as image data for each part of the fundus by color imaging of the fundus image FB, i.e. the image concentration data for each component.

Thus, the concept of the reflectivity ratio equivalent (reflected light intensity ratio) R1 for the G component described below is defined by dividing the light reflected amount $Irg$ of the G component by the total sum of the reflected light amount of the respective components.

$$R1 = Irg/(Irr + Irg + Irb) \quad (4)$$

In similar fashion, the concept of the reflectivity radio equivalent (reflected light intensity ratio) R2 for the B component and the concept of the reflectivity radio equivalent (reflected light intensity ratio) R3 for the R component are defined.

$$R2 = Irb/(Irr + Irg + Irb) \quad (5)$$

$$R3 = Irr/(Irr + Irg + Irb) \quad (6)$$

Equation (4) can be rewritten into the following equation using equations (1) to (3).

$$R1 = (Ig \times Rg)/(Ir \times Rr + Ig \times Rg + Ib \times Rb) \quad (7)$$

$$= Rg/(a \times Rr + Rg + b \times Rb)$$

a where the coefficients a and b are defined by the following equations.

$a = Ir/Ig$ (ratio of the incident light amount of R component to the incident light amount of G component)

$b = Ib/Ig$ (ratio of the incident light amount of B component to the incident light amount of G component)

$$R2 = (Ib \times Rb)/(Ir \times Rr + Ig \times Rg + Ib \times Rb) \quad (8)$$

$$= Rb/(c \times Rr + d \times Rg + Rb)$$

where the coefficients c and d are defined by the following equations.

$c = Ir/Ib$ (ratio of the incident light amount of R component to the incident light amount of B component)

$d = Ig/Ib$ (ratio of the incident light amount of G component to the incident light amount of B component)

$$R3 = (Ir \times Rr)/(Ir \times Rr + Ig \times Rg + Ib \times Rb) \quad (9)$$

$$= Rr/(Rr + e \times Rg + f \times Rb)$$

where the coefficients e and f are defined by the following equations.

e=Ig/Ir (ratio of the incident light amount of G component to the incident light amount of R component)

f=Ib/Ir (ratio of the incident light amount of B component to the incident light amount of R component)

Assuming that the illumination is derived from a white light source having an equal incident light amount for R, G, B components, the coefficients a to f can be considered equal to each other and unity unless there are color irregularities. Even for a light source having unequal incident light amounts of R, G, B, the ratio between them is constant assuming that the same light source is used for imaging and the balance between R, G, B is not changed during the measurement.

The reflectivity ratio equivalents R1, R2 and R3 are numerical values which are not affected by the illumination irregularities of the incident light. The reason is that even in the case where the light amount of the illumination light is different for a different part of the fundus due to the illumination irregularities, the effect of the illumination irregularities is obviated by dividing the incident light amount for each part of the fundus.

In view of this, a program for calculating equations (7) to (9) is prepared and incorporated into a processing circuit constituting the arithmetic means of the personal computer 9, and the calculation of the reflectivity ratio equivalents R1, R2, R3 is carried out for each part of the fundus thereby to reconstruct the fundus image. Then, the fundus image can be displayed free of the effect of the illumination irregularities which may exist.

Specifically, for each part of the fundus image photographed by the color fundus camera, the G component image data corresponding to the reflected light intensity of the G component or the B component image concentration data corresponding to the reflected light intensity of the B component is divided by the sum of the G component image concentration data, the B component image concentration data and the R component image concentration data corresponding to the reflected light intensity of the R component. Then, the reflected light intensity ratio data can be obtained. The area of each part of the fundus image FB desirably corresponds to the area of each pixel of the CCD.

Figure 3:
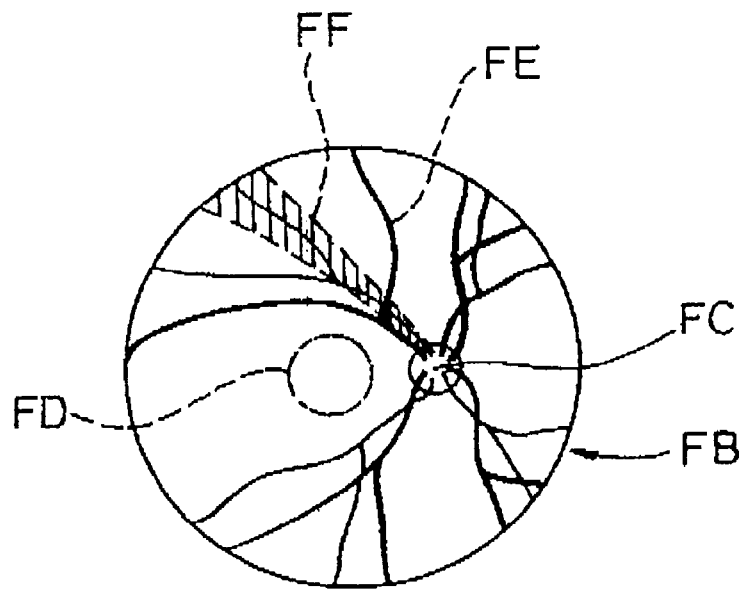
FIG. 3 is a diagram schematically showing an example of a fundus image after being processed.

FIG. 3 is a diagram schematically showing a fundus image obtained by the arithmetic processing described above. The portion FF where the optic nerve fiber layer is lost is indicated by slanted lines.

Figure 4:
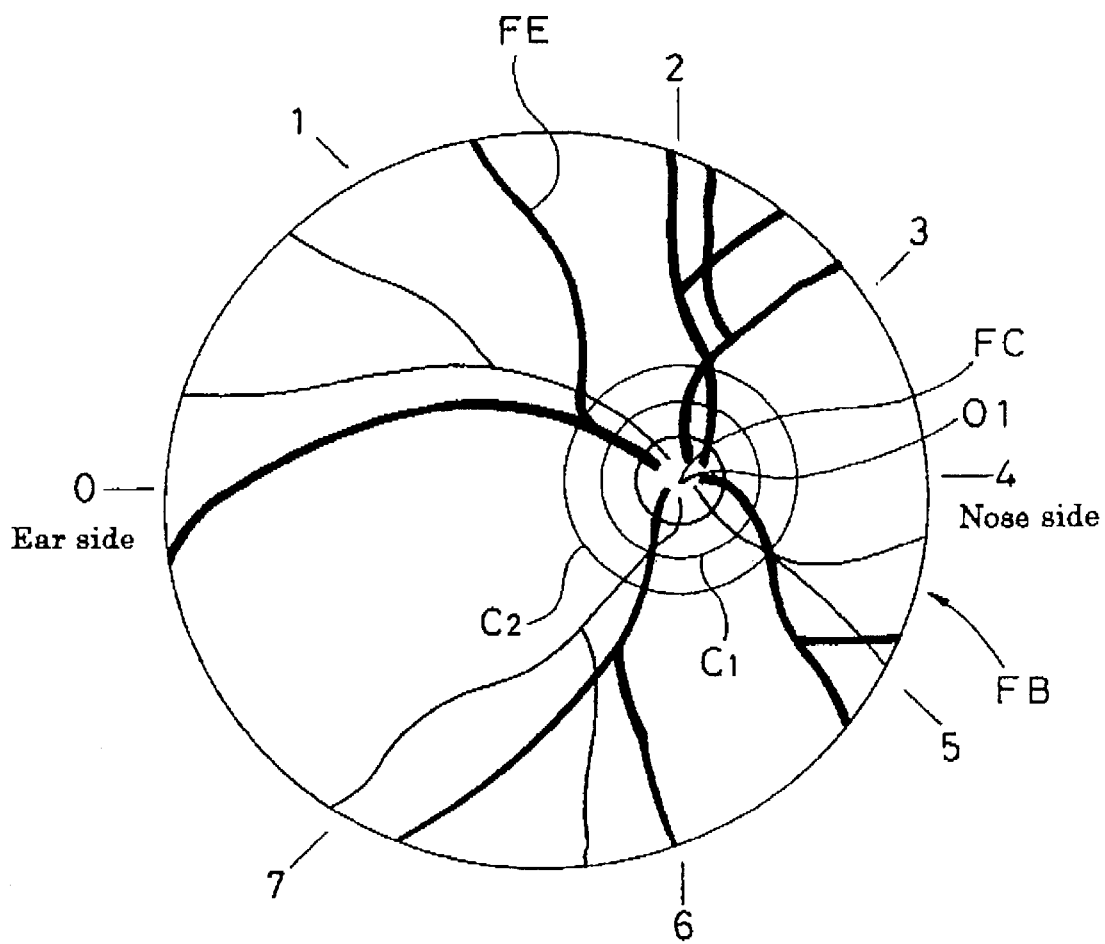
FIG. 4 is a diagram schematically showing a fundus image used for explaining the integration process of the reflected light intensity ratio data along the radial direction.
Figure 5:
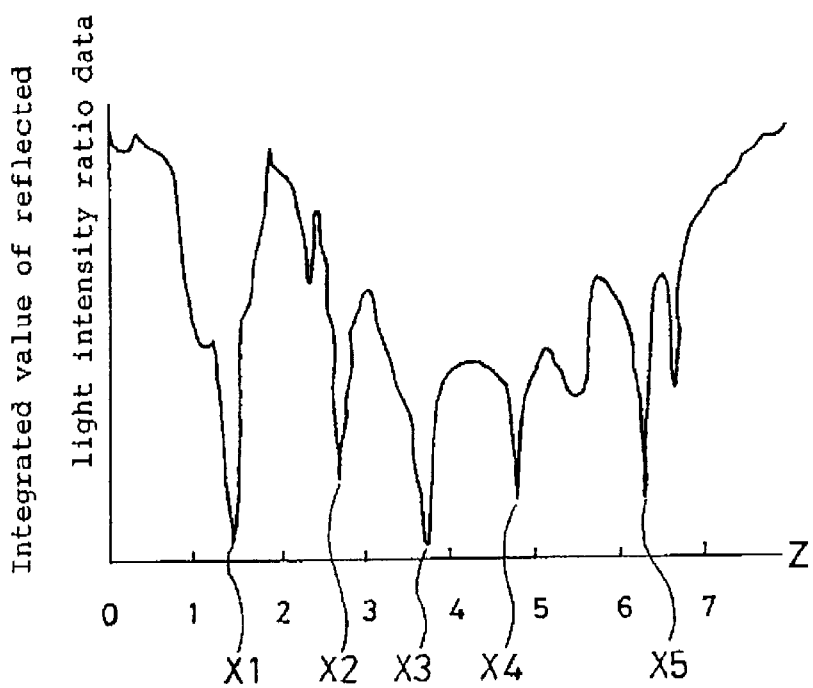
FIG. 5 is a graph showing the result of integration process of the reflected light intensity ratio data.

As an alternative, as shown in FIG. 4, two concentric circles C1, C2 of different radii are plotted in radial direction about the center 01 of a papilla FC, and the operation of integrating the reflected light intensity ratio data is performed in the radial direction circulating around the papilla FC with the first circle C1 as an origin and the second circle C2 as an ending point along the radial direction within the area defined by the concentric circles C1, C2, and the result of this integration processing is displayed in a graph. FIG. 5 is a graph obtained by such a processing.

In the portions where the optic nerve fiber layer is thick, the reflected light intensity ratio data value is large and so is the integration value and in the portions where the optic nerve fiber layer is thin, the reflected light intensity ratio data value is small and so is the integration value. In FIG. 5, numeral "0" indicates the ear side, numeral "4" the nose side, and numerals "0" to "7" indicate the direction of integration processing performed by rotating on the fundus image of FIG. 5 clockwise by 45 degrees each time, which is plotted along the abscissa. The angle from a line O1- "0" is the Z axis. Numerals X1 to X5, on the other hand, designate blood tube portions, in which the reflection intensity of the G and B components is so low that the reflected light intensity ratio data is small in value. Especially, the blood tube portion indicated by numerals X1 and X3 are very thick and therefore is accompanied by a considerable decrease in the reflected light intensity ratio data value.

Figure 6:
FIG. 6 is a graph showing the result of integration process of the reflected light intensity ratio data except for the image portion corresponding to blood tubes.
Figure 7:
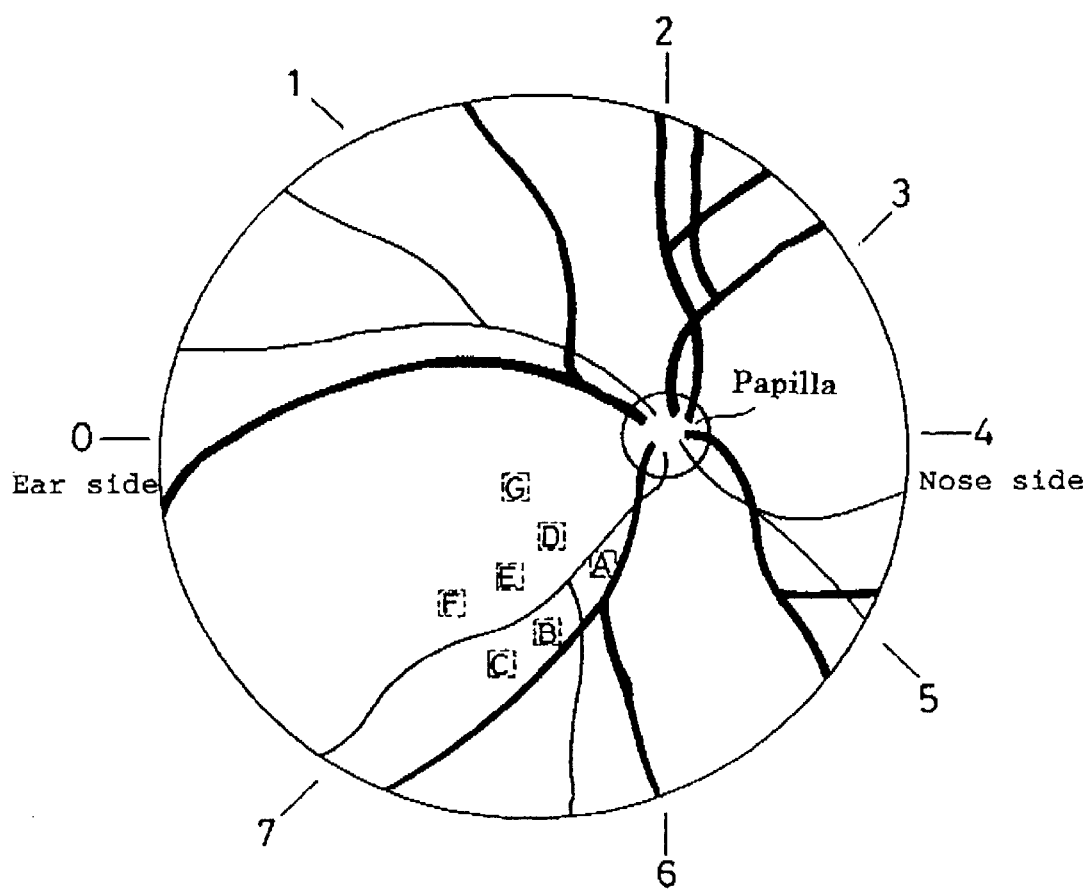
FIG. 7 is a diagram schematically showing a fundus image.

With a graph having the blood tube portions as described above, it is not easy to determine quickly and simply whether the optic nerve fiber layer has a lost portion or not. Thus, the blood tube portions are removed by image filtering. An example of the image processing using the Gabor (or DOG) filter is shown. The general formula of the Gabor filter is given as $$DOG\{\sigma e, \sigma i\} = [1/2\pi] \cdot 1/2\{\sigma e \cdot \exp(-x/2\sigma e)2 - \sigma i \cdot \exp(-x/2\sigma i)2\}$$

where $\sigma e$, $\sigma i$ are the dispersion of normal distribution, and $\sigma e < \sigma i$. Using this DOG filter, the images processing for multiplying the reflected light intensity ratio by the DOG filter for each Z position is performed along Z direction. Then, as shown in FIG. 6, a thickness equivalent graph G1 is obtained in which the decrease by the blood tube portions is interpolated. When a thickness equivalent graph G2 corresponding to the standard thickness of an ordinary fundus fiber layer of a healthy person is also displayed in FIG. 6, presence of the optic nerve fiber layer loss can be determined by comparison of both thickness change graphs of the fundus fiber layer of the healthy person and that of the patient. It is desirable that thickness equivalent graph G2 thus obtained is stored in a database so as to be selected according to age, race, etc.

In this way, for a chronic loss of the optic nerve fiber layer which is very difficult to discover, when a comparison of the optic nerve fiber layer thickness equivalent graph of the patient to the standard optic nerve fiber layer thickness equivalent graph is made and it shows generally low value, a possibility of existence of the chronic loss of the optic nerve fiber layer can be determined.

This is also useful in that the attention of the doctor is called at the time of diagnosis.

According to the embodiments of the invention described above, the reflected light amount of each of the R, G and B components is divided by the total reflected light amount of each of the R, G and B components in order to determine the reflectivity ratio for each part of the fundus. Nevertheless, reflectivity ratio of the R component of the glaucoma patient is considered to be substantially the same as a healthy person.

Figure 8:
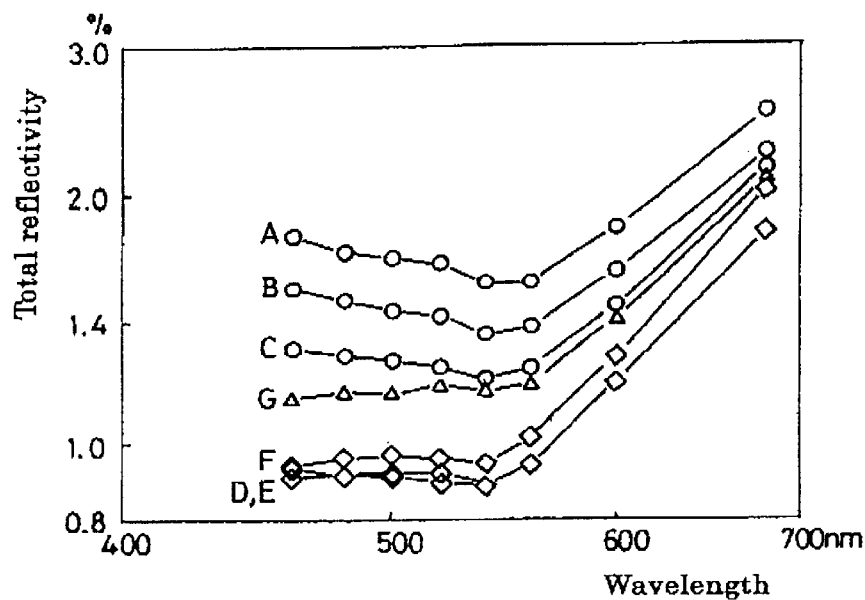
FIG. 8 is a graph showing the reflectivity in each area of the fundus image of FIG. 7 with the wavelength plotted along the abscissa.
Figure 9:
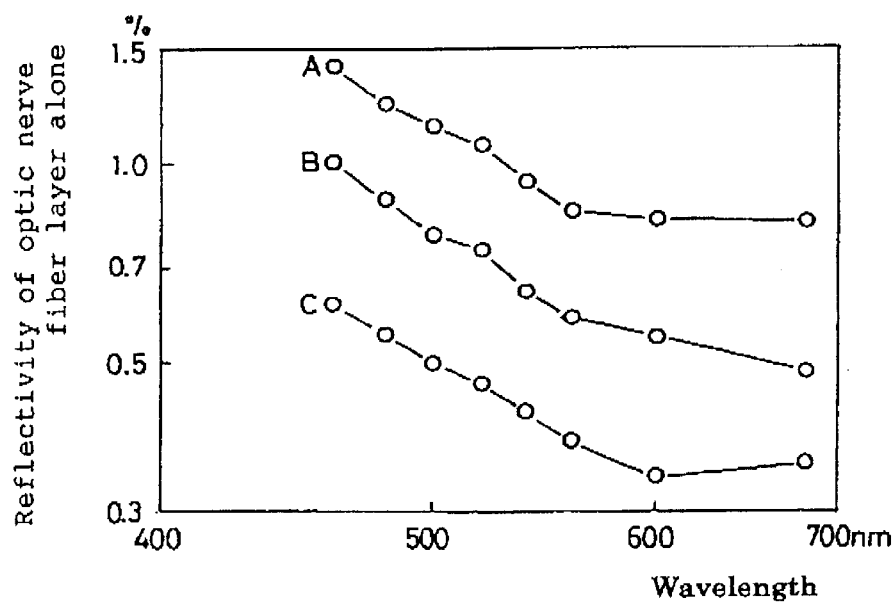
FIG. 9 is a graph showing the reflectivity in the areas A to C of the fundus image of FIG. 7 with the reflectivity for the optic nerve fiber layer only plotted along the wavelength as abscissa.

This is because of the fact that the light of G and B components are mainly reflected on the optic nerve fiber layer and therefore is greatly affected by the loss of the optic nerve fiber layer, while the light of the R component, on the other hand, has characteristics that it is not substantially affected by the presence or absence of the optic nerve fiber layer. The desirability of division by the R component is substantiated also from the graph of FIG. 8. Specifically, the reflectivity ratio of the R-component remains substantially unchanged between the areas A to C and G having the fundus fiber layer and the areas D to F having no fundus fiber layer, while the reflectivity of the G and R components in the areas A to C and G is apparently different from that in the areas D to F having no fundus fiber layer.

By dividing the reflected light amount of the G or B component by the reflected light amount of the R component and thus by determining the reflectivity ratio of the G or B component for each part of the fundus, therefore, a result can be obtained in which the effect of the illumination irregularities is eliminated. In more general, it is desirable that the glaucoma diagnosis is made based on the reflected light intensity ratio data obtained by dividing the image data corresponding to the reflection intensity of the light of shorter wavelength by the image data corresponding to the reflection intensity of the light of longer wavelength.

By this arrangement, the arithmetic program can be simplified and the arithmetic processing speed can be improved further.

The foregoing description refers only to the spectrometry of the illumination light. Assuming that the spectral reflectivity of the whole fundus is $R(\lambda)$, the spectral intensity distribution of the light source is $IO(\lambda)$, and the spectral sensitivity of the R, G, B components of the CCD are $DR(\lambda)$, $DG(\lambda)$, $DB(\lambda)$, respectively, the image signals SR, SG, SB of the R, G, B components obtained from the CCD are given as $$SR = KR \int DR(\lambda) \cdot R(\lambda) \cdot IO(\lambda) d\lambda$$

$$SG = KG \int DG(\lambda) \cdot R(\lambda) \cdot IO(\lambda) d\lambda$$

$$SB = KB \int DB(\lambda) \cdot R(\lambda) \cdot IO(\lambda) d\lambda$$

where $\lambda$ is the wavelength of the light, KR, KG, KB are proportionality constants for the respective components, and the integration is carried out from the lower limit value of wavelength (short wavelength) toward the upper limit value of wavelength (long wavelength).

By determining the reflection intensity ratio data using these image signals SR, SG, SB, the correlation between the thickness of the optic nerve fiber layer and the reflection intensity ratio data can be improved even more accurately.

As described above, in accordance with the present invention, a glaucoma diagnosis apparatus is provided in which the difficulty of glaucoma diagnosis caused by the illumination irregularities on the fundus can be solved.

What is claimed is:

1. A glaucoma diagnosis apparatus, wherein image data corresponding to a reflection intensity of a light of short wavelength is divided by image data corresponding to a reflection intensity of a light of longer wavelength to produce reflected light intensity ratio data for each part of a fundus image photographed by a color fundus camera, and glaucoma is diagnosed based on the reflected light intensity ratio data.

2. A glaucoma diagnosis apparatus, wherein image data corresponding to a reflection intensity of a light of short wavelength is divided by image data corresponding to a reflection intensity of a light containing a light of longer wavelength to produce reflected light intensity ratio data for each part of a fundus image photographed by a color fundus camera, and glaucoma is diagnosed based on the reflected light intensity ratio data.

3. A glaucoma diagnosis apparatus, wherein G component image data corresponding to a reflected light intensity of a G component of light or B component image data corresponding to a reflected light intensity of a B component of light is divided by a sum of the G component image data, the B component image data and R component image data corresponding to a reflected light intensity of a R component of light, and glaucoma is diagnosed based on the reflected light intensity ratio data.

4. A glaucoma diagnosis apparatus, wherein G component image data corresponding to a reflected light intensity of a G component or B component image data corresponding to a reflected light intensity of a B component is divided by R component image data corresponding to a reflected light intensity of a R component to produce reflected light intensity ratio data, and glaucoma is diagnosed based on the reflected light intensity ratio data.

5. A glaucoma diagnosis apparatus comprising arithmetic means for calculating reflected light intensity ratio data in such a manner that G component image data corresponding to a, reflected light intensity of a G component or B component image data corresponding to a reflected light intensity of a B component is divided by a sum of the G component image data, the B component image data and R component image data corresponding to a reflected light intensity of a R component for each part of a fundus image photographed by a color fundus camera for glaucoma diagnosis.

6. A glaucoma diagnosis apparatus comprising arithmetic means for calculating reflected light intensity ratio data in such a manner that G component image data corresponding to a reflected light intensity of a G component or B component image data corresponding to a reflected light intensity of a B component is divided by R component image data corresponding to a reflected light intensity of a R component for each part of a fundus image photographed by a color fundus camera for glaucoma diagnosis.

7. The glaucoma diagnosis apparatus according to any one of claims 1, 2, 5, or 6, wherein the fundus image photographed by the fundus camera is obtained by a white light illumination.

8. The glaucoma diagnosis apparatus according to any one of claims 1, 2, 5, or 6, wherein an area of each part of the fundus image corresponds to an area of each pixel of a CCD.

9. The glaucoma diagnosis apparatus according to claim 5 or 6, wherein glaucoma is diagnosed by performing image processing for removing a blood tube portion of the fundus image.

10. The glaucoma diagnosis apparatus according to claim 5 or 6, wherein image processing is performed in such a manner that two concentric circles of different radii are plotted along a radial direction about a papilla, and the reflected light intensity ratio data are integrated along the radial direction up to a second circle of the two concentric with a first circle of the two concentric circles as an origin.

11. A glaucoma diagnosis recording medium for recording a program for calculating reflected light intensity ratio data in such a manner that G component image data corresponding to a reflected light intensity of a G component or B component image data corresponding to a reflected light intensity of a B component is divided by a sum of the G component image data, the B component image data and R component image data corresponding to a reflected light intensity of a R component for each part of a fundus image photographed by the color fundus camera.

12. A glaucoma diagnosis recording medium for recording a program for calculating reflected light intensity ratio data in such a manner that G component image data corresponding to a reflected light intensity of a G component or B component image data corresponding to a reflected light intensity of a B component is divided by R component image data corresponding to a reflected light intensity of a R component for each part of a fundus image photographed by the color fundus camera.

13. The glaucoma diagnosis apparatus according to claim 7, wherein an area of each part of the fundus image corresponds to an area of each pixel of a CCD.

* * * * *